United States Patent
Boussignac et al.

(10) Patent No.: US 6,761,172 B2
(45) Date of Patent: Jul. 13, 2004

(54) DEVICE FOR RESPIRATORY ASSISTANCE

(76) Inventors: Georges Boussignac, 1, Avenue de Provence, 92160 Antony (FR); Jean-Claude Labrune, 19A, Rue Massenet, 92310 Sevres (FR)

( * ) Notice: Subject to any disclaimer, the term of this patent is extended or adjusted under 35 U.S.C. 154(b) by 0 days.

(21) Appl. No.: 10/369,498

(22) Filed: Feb. 21, 2003

(65) Prior Publication Data

US 2003/0159696 A1 Aug. 28, 2003

(30) Foreign Application Priority Data

Feb. 27, 2002 (FR) .............................................. 02 02468

(51) Int. Cl.[7] ............................................. A61M 16/00
(52) U.S. Cl. .............................. 128/207.14; 128/207.15
(58) Field of Search ........................ 128/200.24, 200.26, 128/204.18, 204.22, 204.23, 204.25, 200.12, 207.14–207.16, 911, 912, 203.12, 203.16, 203.17, 203.18, 204.24, 204.21, 200, 12; 600/531, 532, 543

(56) References Cited

U.S. PATENT DOCUMENTS

| | | | |
|---|---|---|---|
| 4,584,998 A | | 4/1986 | McGrail |
| 5,036,847 A | | 8/1991 | Boussignac et al. |
| 5,452,715 A | * | 9/1995 | Boussignac ............ 128/207.15 |
| 6,273,087 B1 | * | 8/2001 | Boussignac et al. ... 128/204.22 |
| 6,363,935 B1 | | 4/2002 | Boussignac |
| 6,516,801 B2 | * | 2/2003 | Boussignac ............ 128/204.24 |

FOREIGN PATENT DOCUMENTS

| | | |
|---|---|---|
| EP | 0390684 | 10/1990 |
| EP | 0692273 | 1/1996 |
| FR | 2782925 | 3/2000 |
| WO | 9317744 | 9/1993 |

* cited by examiner

Primary Examiner—Teena Kay Mitchell
(74) Attorney, Agent, or Firm—Stevens, Davis, Miller & Mosher, LLP.

(57) ABSTRACT

A device for respiratory assistance includes a tube that may include a deflection section and at least one distribution orifice located downstream of the deflection section. The at least one distribution orifice opens into a main channel of the tube opposite an oblong pressure zone and is for being supplied with a medical fluid.

5 Claims, 2 Drawing Sheets

DEVICE FOR RESPIRATORY ASSISTANCE

FIELD OF THE INVENTION

The present invention relates to a device for respiratory assistance allowing emergency medical care to be provided efficiently to a patient who is in danger of dying.

BACKGROUND OF THE INVENTION

It is known, for example in the case of cardiac arrest, to attempt to resuscitate a patient by massage and, in order to increase the efficacy of this massage, said patient is administered a vasoconstrictive medicine such as adrenaline. This medicine is administered either intravenously or through an endotracheal tube. In the first case, the medicine is relatively slow to arrive at the lungs, while in the second case the medicine disperses and does not necessarily reach said lungs.

Moreover, document EP-0 390 684 has already disclosed a device for respiratory assistance in the form of a tube which can be introduced into the mouth or the nose of a patient and which, in addition to the main channel formed by the tube, comprises at least one auxiliary channel, for example formed in the wall of said tube, permitting injection of a jet of respirable gas (oxygen, air, or mixture of oxygen and air) intended to ventilate the patient, these auxiliary channels opening into the main channel in proximity to the distal end of the latter.

To ensure that the jets of respirable gas do not directly strike the mucosa of the patient under ventilation, risking traumatizing said mucosa on account of their kinetic energy, provision is made, in this known device, that at least the distal end of said auxiliary channels opening into the main channel is parallel thereto and that, opposite the distal orifice of each auxiliary channel, there are deflection means for deflecting said jets of respirable ventilation gas toward the inside of said main channel.

Thus, the jets of respirable gas passing through said auxiliary channels are deflected toward the axis of the main channel when they enter the latter. Experimental measures have shown that, downstream of said deflection means, a pressure zone of oblong shape forms inside said main channel, starting at the points where said auxiliary channels open into the main channel, and continuing in the axial direction along the axis of said main channel with progressive reduction in its cross section, so as to occupy only the central part of the main channel, but that the pressure of said jets of respirable gas drops downstream of said zone of high pressure and the jets of gas pass at low pressure through the distal orifice of the tube. Experience has also shown that, downstream of the distal outlet of the tube, the pressure is low and is maintained constant throughout the respiratory space. This pressure is dependent on the flowrate of respirable gas in the auxiliary channels. Consequently, with the device for respiratory assistance in accordance with the above document, it is possible for example to supply oxygen or a mixture of air and oxygen directly to a patient's lungs, at the level of the carina, and thereby eliminate the dead space which exists in the other known probes and which is approximately a third of the total respiratory volume for an adult and about half for premature neonates. The elimination of this dead space corresponds to an increase in performance of the respiratory cycle of more than 25% in all patients and of nearly 50% in certain cases.

The device in document EP-0 390 684 is therefore particularly advantageous.

SUMMARY OF THE INVENTION

The object of the present invention is to improve this known device in order to allow it to administer medicines efficiently, not only to solve the problem of administering a vasoconstrictor in the event of a cardiac emergency, as was mentioned above, but also in all cases where this is useful.

To this end, according to the invention, the device for respiratory assistance comprising a tube which forms a main channel and which is intended to be connected via its distal end to an airway of a patient so that said main channel connects said patient's respiratory system to the outside, said device further comprising at least one auxiliary channel which is connected, at its proximal end, to a source of respirable gas in order to be able to insufflate a jet of this respirable gas into said respiratory system and whose distal end opens into said main channel in proximity to the distal end of the latter, deflection means for deflecting said jet of respirable ventilation gas in the direction of the axis of said main channel being provided opposite the distal orifice of said auxiliary channel in such a way that, downstream of said deflection means, a pressure zone of oblong shape forms inside said main channel, starting at said distal orifice and continuing in the distal direction along the axis of said main channel, with progressive reduction of its cross section as it moves away from the inner wall of said main channel and comes to occupy only the central part of the latter, is distinguished by the fact that said tube comprises, downstream (relative to said jet of respirable gas) of said deflection means, at least one distribution orifice which opens into said main channel opposite said oblong pressure zone and which can be supplied with a medical fluid.

Thus, by virtue of the present invention, the medical fluid, which can be a gas or liquid, is nebulized and delivered directly to the lungs of the patient under ventilation exactly like the respirable ventilation gas, while said lungs are inflated by means of this ventilation. The injection of the medical fluid thus affects the totality of the surface of said lungs, so that said fluid can have the maximum efficacy.

Said orifice for distribution of medical fluid is preferably connected to the proximal end of said tube via a channel which is provided within the thickness of said tube and by way of which it is supplied with medical fluid.

In the case where, in order to avoid using a source of respirable gas at high pressure, the device according to the present invention comprises, as is described in the document U.S. Ser. No. 09/387,790, a ring arranged in said main channel downstream (relative to said jet of respirable gas) of said deflection means and surrounding said oblong pressure zone and at least partially obturating the peripheral space of said main channel located between said inner wall of the latter and said oblong pressure zone, it is advantageous that said ring is arranged between said distribution orifice and said deflection means.

Moreover, in order to further increase the efficacy of the device according to the present invention, it is preferable that the supply of medical fluid to said distribution orifice is interrupted during the patient's exhalations, so that said medical fluid is introduced into the latter's lungs only during inhalations.

BRIEF DESCRIPTION OF THE DRAWINGS

The figures in the attached drawing will make it clear how the invention can be realized. In these figures, identical reference numbers designate similar elements.

DETAILS OF DESCRIPTION

Figure 1:
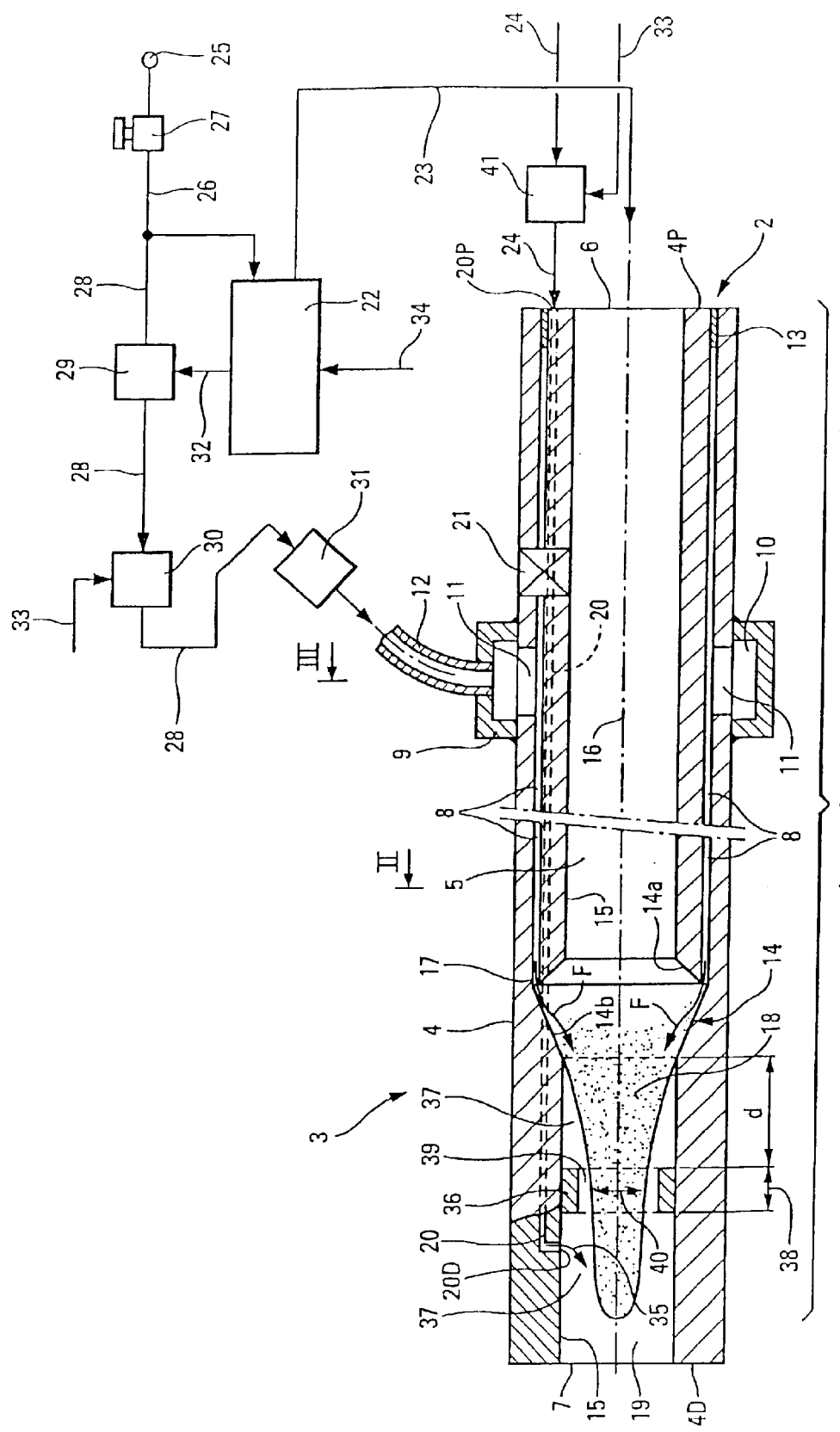
FIG. 1 is a diagrammatic and partial view, in an enlarged axial section, of an embodiment of the device of the invention.

FIG. 1 shows, diagrammatically and on an enlarged scale, only the proximal end 2 and distal end 3 of an embodiment 1 of the device according to the invention. This embodiment can for example constitute an oronasal endotracheal probe with or without balloon, a pediatric endotracheal probe, a gas-monitoring probe, an endobronchial probe, a nasopharyngeal probe, an anatomical intubation probe for infants, a neonatal Cole probe, a Gedel cannula probe, a nasal probe for oxygen therapy, a nasal or bucconasal mask or a nasal balloon for treating sleep apnea.

The device 1 comprises a tube 4 which is flexible or preformed (to adapt to the morphology of the patient) and delimits a main channel 5 opening out via the orifice 6 at the proximal end 2 and via the orifice 7 at the distal end 3.

Thus, the main channel 5 is able to ensure passage between the orifices 6 and 7, one of which (the distal orifice 7) is intended to be located inside a patient's airways, and the other of which (the proximal orifice 6) is intended to be located outside said patient. This proximal orifice 6 can open out to the surrounding air and, in this case, the patient can breathe in fresh air and exhale vitiated air through the main channel 5. It is also possible, as is explained below, to connect the orifice 6 to a source of pressurized respirable gas and to provide a system of one-way valves so that the patient inhales the respirable gas from said source via said main channel 5 and exhales the vitiated gas to the surrounding air, again via this main channel.

The diameter of the main channel 5 is of the order of several millimeters. Satisfactory tests have been conducted with diameters of 3 mm, 7 mm, 8 mm and 12 mm.

Moreover, auxiliary channels 8, formed in the thickness of the wall of the tube 4, extend along almost the entire length of the main channel 5 and are intended to be connected to a source of pressurized respirable gas, as is described below.

The connection to the source of pressurized respirable gas can be effected by means of a ring 9, surrounding the tube 4 in a leaktight manner, at the proximal end 2, and delimiting a leaktight annular chamber 10 about said tube. The auxiliary channels 8 communicate with the chamber 10 by way of local cutouts 11 in the wall of the tube 4, and said chamber 10 is connected to said source of respirable gas via a conduit 12. Of course, the proximal ends of the channels 8 are obturated, for example by plugs 13 introduced from the proximal end face 4P of the tube 4.

The auxiliary channels 8 have a smaller diameter than that of the main channel 5. The diameter of the auxiliary channels 8 is preferably less than 1 mm and advantageously it is of the order of 400 through 800 microns. At the distal end, the auxiliary channels 8 open into a recess 14 of the inner wall 15 of the tube 4. The recess 14 is annular and is centered on the axis 16 of the distal end 3. It comprises a face 14a which is substantially transverse or slightly inclined in such a way as to constitute a widening of the main channel 5 into which said auxiliary channels 8 open via their orifices 17, and a face 14b which follows the face 14a and converges in the direction of the axis 16.

Thus, when the auxiliary channels 8 are supplied with pressurized respirable gas via the elements 9 through 12, the corresponding jets of gas strike the inclined face 14b, which deflects them in the direction of the axis 16 (arrows F in FIG. 1), generating, inside the distal end 3 of the main channel 5, a pressure zone 18 of oblong shape starting at said distal orifices 17 and continuing in the direction of the distal orifice 7 along the axis 16 of said distal end 3. The cross section of the pressure zone 18 decreases progressively from the recess 14 toward the distal orifice 7, said pressure zone 18 moving progressively away from the inner wall 15 of the tube 4 and coming to occupy only the central part of the distal end 3 of the latter. Downstream of the pressure zone 18, the jets of respirable gas which have been deflected generate a low-pressure zone 19 in proximity to the axis 16, promoting gas circulation inside the main channel 5 from the proximal orifice toward the distal orifice. This therefore promotes inhalation by the patient.

At least one supplementary channel 20 is provided in the thickness of the tube 4. This supplementary channel 20 comprises a proximal orifice 20P opening out in the proximal end face 4P of said tube 4, and a distal orifice 20D formed in the inner wall 15 of said tube 4 and opening into the main channel 5 opposite the pressure zone 18. The supplementary channel 20 can be supplied with pressurized medical fluid—gas or liquid—via its proximal orifice 20P, by way of a conduit 24 connected to a source (not shown) of such fluid. A controllable valve 41 is mounted on the conduit 24.

For safety purposes, a calibrated relief valve 21 can be provided in the proximal end 2 of the tube 4. Thus, in the event of accidental overpressure in the main channel 5, an escape of gas is produced outside the patient, through the wall of the tube 4, in order to instantly eliminate this overpressure.

Figure 3:
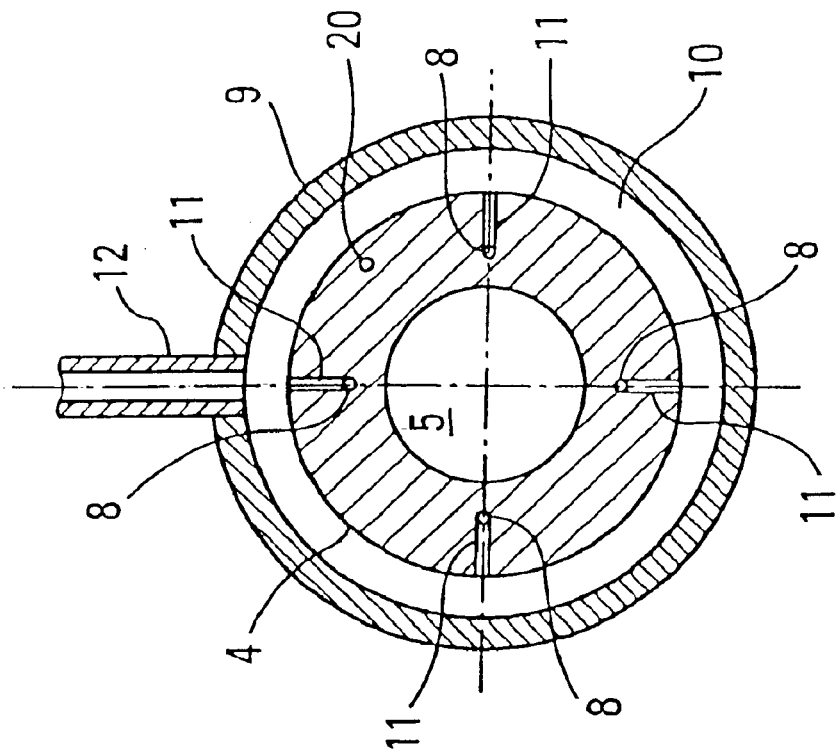
FIGS. 2 and 3 are transverse sections along the lines II—II and III—III, respectively, in FIG. 1.
Figure 2:
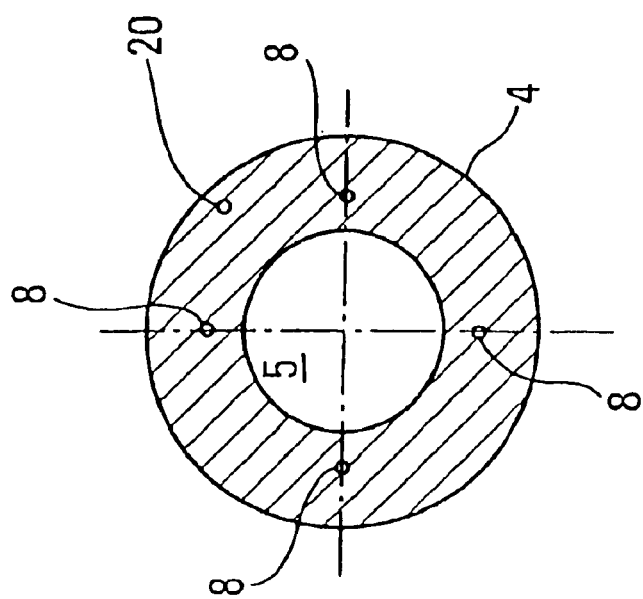

As FIGS. 2 and 3 show, the auxiliary channels 8 are arranged regularly about the axis of the tube 4. Their number can vary depending on the use (for adults or children), but it is generally between three and nine.

The tube 4 of the device according to the invention can be made of any material already used in respiratory probes, for example a polyvinyl chloride, with an optional coating of silicone or steel permitting the injections at high pressure.

Of course, the dimensions of the device according to the invention can vary considerably, mainly depending on the way in which the tube is fitted and on the size of the patient, who may be an adult, a child, a newborn infant or a premature baby.

The device 1 additionally comprises a supply and control device 22 which is connected to the proximal orifice 6 of the tube 4 via a connection 23 and which can be controlled by a pressure sensor (not shown) via a connection 34. The pressure-tapping point of this latter sensor can be arranged in the distal face 4D.

The supply and control device 22 is supplied with pressurized respirable gas from a source 25, to which it is connected via a conduit 26 on which a controllable pressure reducer/flow meter 27 is mounted.

The outlet of the pressure reducer/flow meter 27 is connected to the conduit 12 via a branch conduit 28 on which a first controllable valve 29, a second controllable valve 30 and a humidifier 31 are mounted in series.

The controllable valve 29 is controlled by the supply and control device 22 by way of a connection 32.

The controllable valve 30 is controlled, via a connection 33, by a pressure sensor (not shown) which is able to detect the change-overs from inhalation to exhalation in the patient's breathing. The measurement point of this pressure sensor can be situated in proximity to the distal orifice 7. The connection 33 also controls the controllable valve 41 for supply of medical fluid.

In the distal end 3 it is possible to arrange a ring 36 surrounding the central pressure zone 18 and at least partially occupying the annular peripheral space 37 located between said central pressure zone 18 and the inner wall 15 of the distal end 3 of the channel 5.

By means of such a ring 36, the pressure from the source of respirable gas 25 necessary for obtaining the pressure zone 18 can be lowered.

As a general rule, the distance d between the ring 36 and the inclined deflection face 14b is close to the diameter of the distal part of the main channel 5.

To make it possible to obtain the required optimum pressure reduction of the source 25, this distance d can be adjusted, as is illustrated by the double arrow 38. It is also advantageous, for the same purpose, for the diameter of the central opening 39 of the ring 36 to be adjustable, as is illustrated by the double arrow 40. This double adjustment can be obtained by virtue of a set of several interchangeable rings 36 which can be mounted sliding in the distal end of the main channel 5, as desired. Alternatively, the ring 36 can be formed by an inflatable ring whose internal diameter can be varied by inflation.

The modes of operation of the device 1 according to the invention are the following:

in the mode for artificial respiration, the supply and control device 22 on the one hand causes the valve 29 to close by way of the connection 32, so that the conduit 12 is not supplied with gas, and, on the other hand, delivers respirable gas into the tube 4 by way of the connection 23. This device 22 includes means (not shown) making it possible to adjust the pressure and the flowrate of respirable gas which it receives from the conduit 26 and which it delivers to the tube 4. If an overpressure forms in the patient's airways, this is detected and transmitted via the connection 34 to the device 22 which arrests its operation. Moreover, if this overpressure, exceeds the calibration threshold of the calibrated valve 21, the latter opens and the proximal channel 5 is brought into communication with the atmosphere;

in the mode for respiratory assistance, the supply and control device 22 cuts the connection 23 in order to bring the proximal orifice 6 into communication with the atmosphere and controls the valve 29 via the connection 32 so that this valve delivers continual or pulsed jets of respirable gas to the patient via the valve 30, the humidifier 31 and the auxiliary channels 8.

The pressure zone 18 and the low-pressure zone 19 thus form, permitting easy ventilation of the patient. Said patient can then inhale freely and deeply. Simultaneously, the valve 41 being open, medical fluid is introduced into the patient's lungs via the conduit 24, the channel 20 and the orifice 20D.

When, after inhalation, the patient begins to exhale, this start of exhalation is detected and the valves 30 and 41 are closed via the connection 33. The jets of respirable gas, the pressure zone 18, the low-pressure zone 19 and the supply of medical fluid thus disappear and the patient can exhale freely through the main channel 5.

If, during ventilation, an overpressure is produced in the patient's airways, as has been described above, this overpressure is detected and transmitted via the supplementary channel 20, so that the device 22 closes the valve 29 and the ventilation is stopped.

From what has been explained above, it will therefore be seen that, by virtue of the invention, it is possible to obtain, using a source of moderate pressure, a respiratory assistance which is effective and reliable, humidified, and accompanied by an injection of medical fluid, permitting almost total disappearance of the dead space inherent to the known probes. Moreover, it will be noted that the respiratory assistance device can be designed to be light and transportable so as to be able to be used in emergencies away from a hospital or clinic.

What is claimed is:

1. A device for respiratory assistance comprising:

a tube which (i) has a distal end and a proximal end and (ii) forms a main channel, extending from said distal end to said proximal end, and at least one auxiliary channel, said tube for being connected via said distal end to an airway of a patient so that said main channel connects said patient's respiratory system to the outside, said at least one auxiliary channel for being connected, at said proximal end, to a source of respirable gas in order to be able to insufflate a jet of this respirable gas into said respiratory system, said at least one auxiliary channel opening at one end into said main channel in proximity to said distal end, and deflection means for deflecting said jet of respirable ventilation gas in a direction of a longitudinal axis of said main channel, said deflection means being provided opposite a distal orifice of said auxiliary channel in such a way that, downstream of said deflection means, a pressure zone of oblong shape forms inside said main channel, starting at said distal orifice and continuing in a direction of said distal end along said axis of said main channel, with progressive cross-sectional reduction of said pressure zone in a direction away from an inner wall of said main channel such that said pressure zone comes to occupy only a central part of said main channel, wherein said tube comprises, downstream of said deflection means, at least one distribution orifice which opens into said main channel opposite said pressure zone and which can be supplied with a medical fluid.

2. The device as claimed in claim 1, wherein said distribution orifice is connected to the proximal end of said tube via a supplementary channel, which is provided within a wall of said tube, and said medical fluid is provided by way of said supplementary channel.

3. The device as claimed in claim 1, further comprising a ring arranged in said main channel downstream of said deflection means and surrounding said oblong pressure zone, at least partially obturating a peripheral space of said main channel located between said inner wall of said main channel and said oblong pressure zone, wherein said ring is arranged between said distribution orifice and said deflection means.

4. A device for respiratory assistance comprising:

means forming a main channel having a distal end and a proximal end, said main channel for being connected via said distal end to an airway of a patient so that said main channel connects said patient's respiratory system to the outside, means forming at least one auxiliary channel for being connected, at said proximal end of said main channel, to a source of respirable gas in order to be able to insufflate a jet of this respirable gas into said respiratory system, said at least one auxiliary channel opening at one end into said main channel in proximity to said distal end, deflection means for deflecting said jet of respirable ventilation gas in a direction of a longitudinal axis of said main channel, said deflection means being provided opposite a distal orifice of said auxiliary channel in such a way that, downstream of said deflection means, a pressure zone of oblong shape forms inside said main channel, starting at said distal orifice and continuing in a direction of said distal end along said axis of said main channel, with progressive cross-sectional reduction of said pressure zone in a direction away from an inner wall of said main channel such that said pressure zone comes to occupy only a central part of said main channel, and means, located downstream of said deflection means, which is in communication with said main channel opposite said pressure zone, for supplying a medical fluid.

5. The device as claimed in claim 4, further comprising a ring arranged in said main channel downstream of said deflection means and surrounding said oblong pressure zone, at least partially obturating a peripheral space of said main channel located between aid inner wall of said main channel and said oblong pressure zone, wherein said ring is arranged between said deflection means and said means for supplying said medical fluid.

* * * * *